(12) United States Patent
Eckhardt

(10) Patent No.: US 7,667,035 B2
(45) Date of Patent: Feb. 23, 2010

(54) IMIDAZOLE DERIVATIVES, THEIR PREPARATION AND THEIR USE AS INTERMEDIATES FOR THE PREPARATION OF PHARMACEUTICAL COMPOSITIONS AND PESTICIDES

(75) Inventor: Matthias Eckhardt, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 12/207,803

(22) Filed: Sep. 10, 2008

(65) Prior Publication Data

US 2009/0023920 A1 Jan. 22, 2009

Related U.S. Application Data

(62) Division of application No. 11/124,798, filed on May 9, 2005, now Pat. No. 7,439,370.

(60) Provisional application No. 60/576,219, filed on Jun. 2, 2004.

(30) Foreign Application Priority Data

May 10, 2004 (DE) ........................ 10 2004 022 970

(51) Int. Cl.
C07D 237/28 (2006.01)
(52) U.S. Cl. ..................................... 544/235
(58) Field of Classification Search ........................ None
See application file for complete search history.

(56) References Cited

U.S. PATENT DOCUMENTS

| | | | |
|---|---|---|---|
| 2,928,833 A | 3/1960 | Leake et al |
| 4,005,208 A | 1/1977 | Bender |
| 4,599,338 A | 7/1986 | Regnier et al. |
| 5,041,448 A | 8/1991 | Janssens |
| 5,051,517 A | 9/1991 | Findeisen |
| 5,223,499 A | 6/1993 | Greenlee |
| 5,234,897 A | 8/1993 | Findeisen et al. |
| 5,258,380 A | 11/1993 | Janssens |
| 5,266,555 A | 11/1993 | Findeisen et al. |
| 5,389,642 A | 2/1995 | Dorsch |
| 5,470,579 A | 11/1995 | Bonte et al. |
| 5,719,279 A | 2/1998 | Kufner-Muhl et al. |
| 5,753,635 A | 5/1998 | Buckman |
| 6,303,661 B1 | 10/2001 | Demuth |
| 6,342,601 B1 | 1/2002 | Bantick |
| 6,548,481 B1 | 4/2003 | Demuth et al. |
| 6,579,868 B1 | 6/2003 | Asano et al. |
| 6,821,978 B2 | 11/2004 | Chackalamannil |
| 6,869,947 B2 | 3/2005 | Kanstrup |
| 7,060,722 B2 | 6/2006 | Kitajima |
| 7,074,794 B2 | 7/2006 | Kitajima |
| 7,074,798 B2 | 7/2006 | Yoshikawa |
| 7,074,923 B2 | 7/2006 | Dahanukar |
| 7,109,192 B2 | 9/2006 | Hauel |
| 7,179,809 B2 | 2/2007 | Eckhardt |
| 7,183,280 B2 | 2/2007 | Himmelsbach |
| 7,192,952 B2 | 3/2007 | Kanstrup |
| 7,217,711 B2 | 5/2007 | Eckhardt |
| 7,235,538 B2 | 6/2007 | Kanstrup et al. |
| 7,407,955 B2 | 8/2008 | Himmelsbach et al. |
| 2002/0161001 A1 | 10/2002 | Kanstrup |
| 2002/0169174 A1 | 11/2002 | Chackalamannil et al. |
| 2002/0198205 A1 | 12/2002 | Himmelsbach |
| 2003/0105077 A1 | 6/2003 | Kanstrup et al. |
| 2003/0199528 A1 | 10/2003 | Kanstrup |
| 2003/0232987 A1 | 12/2003 | Dahanukar et al. |
| 2003/0236272 A1 | 12/2003 | Carr |
| 2004/0034014 A1 | 2/2004 | Kanstrup et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1 | 5/2004 | Himmelsbach et al. |
| 2004/0116328 A1 | 6/2004 | Yoshikawa et al. |
| 2004/0122228 A1 | 6/2004 | Maier |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |

(Continued)

FOREIGN PATENT DOCUMENTS

CA 2136288 A1 5/1995

(Continued)

OTHER PUBLICATIONS

Rhee et al, J. Am. Chem. Soc. 1990, 112, 8174-8175.*

(Continued)

*Primary Examiner*—Kamal A Saeed
(74) *Attorney, Agent, or Firm*—Michael P. Morris; Mary-Ellen M. Devlin; David L. Kershner

(57) ABSTRACT

The invention relates to new substituted imidazoles of general formula

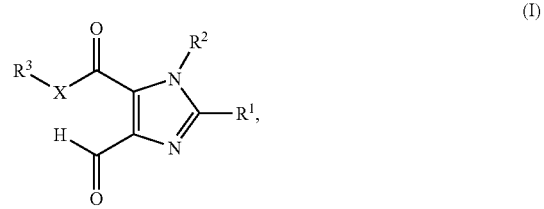

(I)

wherein $R^1$ to $R^3$ and X are defined as in the claims, the tautomers, the enantiomers, the diastereomers, the mixtures thereof and the salts thereof, and processes for preparing them and their use as intermediates for preparing pharmaceutical compositions or pesticides.

2 Claims, No Drawings

U.S. PATENT DOCUMENTS

| | | |
|---|---|---|
| 2005/0130985 A1 | 6/2005 | Himmelsbach |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0219178 A1 | 9/2007 | Muramoto |
| 2007/0259900 A1 | 11/2007 | Sieger et al. |
| 2007/0281940 A1 | 12/2007 | Dugi |
| 2008/0107731 A1 | 5/2008 | Kohlrausch et al. |
| 2008/0249089 A1 | 10/2008 | Himmelsbach et al. |
| 2008/0255159 A1 | 10/2008 | Himmelsbach et al. |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 2002/02560 A2 | 1/2002 |
| WO | 2002/14271 A1 | 2/2002 |
| WO | 2002/24698 A1 | 3/2002 |
| WO | 2002/068420 A1 | 9/2002 |
| WO | 2003/004496 A1 | 1/2003 |
| WO | 2003/024965 A2 | 3/2003 |
| WO | 2003/057200 A2 | 7/2003 |
| WO | 2003/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/096806 A1 | 11/2004 |
| WO | 2004/108730 A1 | 12/2004 |
| WO | 2004/050658 A1 | 6/2005 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |

OTHER PUBLICATIONS

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthéses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," Pnas 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective:" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β -Cell Survival and Islet Neogenesis in Streptozotocin-Induced Diabetic Rats; Diabetes, vol. 52, Mar. 2003 pp. 741-750.

Rhee, et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A., et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S., et al; "Suppression of Arthritis by the Inhibitors of Dipeptidyl Peptidase IV," In. J. Immunopharmac., vol. 19, No. 1, pp. 15-24, 1997.

Wolff, M.E.; "Burger's Medicinal Chemistry and Drug Discovery" Fifth Edition, vol. 1: Principles and Practice, pp. 975-977, 1994, John Wiley & Sons, Inc.

Yoshikawa, Seiji et al.: Chemical Abstract of Japanese Patent No. WO 2003/104229 Preparation of purinone derivatives as dipeptidylpeptidase IV (DPP-IV) inhibitors.

Zhong, Qing et al; "Glucose-dependent insulinotropic peptide stimulates proliferation and TGF-βrelease from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

* cited by examiner

IMIDAZOLE DERIVATIVES, THEIR PREPARATION AND THEIR USE AS INTERMEDIATES FOR THE PREPARATION OF PHARMACEUTICAL COMPOSITIONS AND PESTICIDES

This Application is a divisional of U.S application Ser. No. 11/124,798 filed on May 9, 2005 now U.S. Pat. No. 7,439,370, which claims benefit under 35 U.S.C. § 119(e) of U.S. provisional Application No. 60/576,219, filed Jun. 2, 2004, which claims priority under 35 U.S.C. § 119 to GERMANY 10 2004 022970 filed May 10, 2004 the entire disclosure of each Application is hereby incorporated by reference.

The present invention relates to new substituted imidazoles of general formula

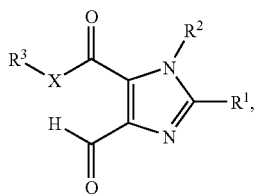

(I)

the tautomers, the enantiomers, the diastereomers, the mixtures thereof and the salts thereof and processes for the preparation thereof. The compounds may be used as intermediates for preparing pharmaceutical compositions or pesticides. Starting from them, other heterocyclic rings may be linked to the imidazole to form important polycyclic basic structures. They are particularly suitable for preparing imidazo[4,5-d]pyridazin-4-ones and imidazo[4,5-c]pyridine-4-ones which may be used, e.g., as DPP IV inhibitors in the treatment of diabetes (cf., e.g., WO 03/104229). Moreover, a broad range of substitutions may be carried out at three positions of the imidazole under different reaction conditions, making these compounds particularly attractive as the scaffold in building up libraries of combinations.

In the above formula I $R^1$ denotes a fluorine, chlorine, bromine, or iodine atom, $R^2$ denotes a $C_{3-8}$-alkyl group, a $C_{1-3}$-alkyl group substituted by a group $R_a$, while $R_a$ denotes a $C_{3-7}$-cycloalkyl group optionally substituted by one or two $C_{1-3}$-alkyl groups, a $C_{3-8}$-cycloalkenyl group optionally substituted by one or two $C_{1-3}$-alkyl groups, an aryl group or a heteroaryl group, a $C_{3-8}$-alkenyl group, a $C_{3-6}$-alkenyl group substituted by a fluorine, chlorine or bromine atom or by a trifluoromethyl group, a $C_{3-8}$-alkynyl group, an aryl group or an aryl-$C_{2-4}$-alkenyl group, X denotes an oxygen or sulphur atom or a nitrogen atom which is substituted by $R_b$, while $R_b$ denotes a hydrogen atom, a hydroxy, aryloxy, arylmethyloxy, heteroaryloxy, heteroarylmethyloxy or $C_{1-10}$-alkyloxy group, while the hydrogen atoms of the alkyloxy group may be wholly or partly replaced by fluorine atoms, a $C_{1-10}$-alkylcarbonyl, arylcarbonyl, heteroarylcarbonyl, $C_{1-10}$-alkyloxy-carbonyl, $C_{1-10}$-alkylaminocarbonyl, di-($C_{1-10}$-alkyl)-aminocarbonyl, $C_{1-10}$-alkylsulphonyl, arylsulphonyl, heteroarylsulphonyl, $C_{1-10}$-alkylsulphinyl, arylsulphinyl or heteroarylsulphinyl group, while the hydrogen atoms of the above-mentioned $C_{1-10}$-alkyl groups may be wholly or partly replaced by fluorine atoms, a $C_{1-10}$-alkyl, $C_{2-10}$-alkenyl, $C_{2-10}$-alkynyl, $C_{3-7}$-cycloalkyl or $C_{5-8}$-cycloalkenyl group, while the hydrogen atoms in the above-mentioned groups may each be wholly or partly replaced by fluorine atoms and in the above-mentioned groups 1 to 4 methylene groups may each be replaced by an oxygen or sulphur atom, by an —NH— or —N($C_{1-3}$-alkyl)- group or by a carbonyl, sulphinyl or sulphonyl group, an aryl group or a heteroaryl group, or $R_b$ and $R^3$ are linked together and are closed up into a ring at the nitrogen atom, while $R_b$ and $R^3$ together denote a $C_{2-7}$-alkylene group, while one or two methylene groups may each be substituted by one or two fluorine atoms or replaced by an oxygen or sulphur atom, by an —NH— or —N($C_{1-3}$-alkyl)- group or by a carbonyl, sulphinyl or sulphonyl group, or a $C_{4-7}$-alkenylene group, while one or two methylene groups may each be substituted by one or two fluorine atoms or replaced by an oxygen or sulphur atom, by an —NH— or —N($C_{1-3}$-alkyl)- group or by a carbonyl, sulphinyl or sulphonyl group and the double bond may be part of an aryl or heteroaryl group anellated to the ring, and $R^3$ denotes a hydrogen atom, a $C_{1-20}$-alkyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, a $C_{1-12}$-alkyl group substituted by a group $R_c$ wherein the hydrogen atoms may be wholly or partly replaced by fluorine atoms and wherein 1 to 4 methylene groups may each be replaced by an oxygen or sulphur atom, by an —NH— or —N($C_{1-3}$-alkyl)- group or by a carbonyl, sulphinyl or sulphonyl group, while $R_c$ denotes a $C_{3-18}$-cycloalkyl group optionally substituted by one or two $C_{1-3}$-alkyl groups wherein the hydrogen atoms may be wholly or partly replaced by fluorine atoms and wherein one to two methylene groups may each be replaced by an oxygen or sulphur atom, by an —NH— or —N($C_{1-3}$-alkyl)- group or by a carbonyl, sulphinyl or sulphonyl group, a $C_{5-18}$-cycloalkenyl optionally substituted by one or two $C_{1-3}$-alkyl groups group wherein the hydrogen atoms may be wholly or partly replaced by fluorine atoms, one to two methylene groups may each be replaced by an oxygen or sulphur atom, by an —NH— or —N($C_{1-3}$-alkyl)- group or by a carbonyl, sulphinyl or sulphonyl group and the double bond may be part of an aryl or heteroaryl group anellated to the ring, an aryl group or a heteroaryl group, a $C_{3-18}$-cycloalkyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, a $C_{3-20}$-alkenyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, a $C_{5-20}$-cycloalkenyl group wherein the hydrogen atoms may be wholly or partly replaced by fluorine atoms and wherein 1 to 4 methylene groups may each be replaced by an oxygen or sulphur atom, by an —NH— or —N($C_{1-3}$-alkyl)-group or by a carbonyl, sulphinyl or sulphonyl group, and wherein the double bond may be part of an aryl or heteroaryl group anellated to the ring, a $C_{3-20}$-alkynyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, an aryl group, a heteroaryl group, an aryl-$C_{2-6}$-alkenyl group or, if X does not represent a nitrogen atom which is substituted by a hydroxy, aryloxy, arylmethyloxy, heteroaryloxy, heteroarylmethyloxy or $C_{1-10}$-alkyloxy group, may also denote an amino group which may be substituted by one or two $C_{1-3}$-alkyl groups, or similarly, if X does not represent a nitrogen atom which is substituted by a hydroxy, aryloxy, arylmethyloxy, heteroaryloxy, heteroarylmethyloxy or $C_{1-10}$-alkyloxy group, may also denote a 3- to 7-membered cycloalkyleneimino group, while one to two methylene groups of the cycloalkyleneimino group may each be replaced by an oxygen atom or a carbonyl, sulphinyl or sulphonyl group, or $R^3$ and X together represent a fluorine or chlorine atom, while by the aryl groups mentioned in the definition of the above groups are meant phenyl or naphthyl groups which may be mono- to pentasubstituted independently of one another by fluorine and chlorine atoms and may be mono-, di- or trisubstituted by $R_d$, while the substituents may be identical or different and $R_d$ denotes a bromine or iodine atom, a trifluoromethyl, cyano, nitro, amino, aminocarbonyl, aminosulphonyl, methylsulphonyl, acetylamino, methylsulphonylamino, $C_{1-4}$-alkyl, $C_{1-3}$-alkyl-carbonyl, cyclopropyl, ethenyl, ethynyl, hydroxy, $C_{1-4}$-alkyloxy, $C_{1-4}$-alkoxy-carbonyl, methylsulphinyl, phenylsulphinyl, methylsulphonyl, phenylsulphonyl, difluoromethoxy or trifluoromethoxy group, by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, and the above-mentioned heteroaryl groups may be mono- to pentasubstituted by fluorine and chlorine atoms and $R_d$ may be mono-, di- or trisubstituted, while the substituents may be identical or different and $R_d$ is as hereinbefore defined, by the cycloalkyl groups mentioned in the above definitions are meant both mono- and polycyclic ring systems, which are either bridged, spiro-bridged or anellated in construction, by the cycloalkenyl groups mentioned in the above definitions are meant both mono- and polycyclic ring systems, which are either bridged or anellated in construction, and have at least one C=C double bond, while, unless otherwise stated, the above-mentioned alkyl, alkenyl and alkynyl groups may be straight-chain or branched, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

Moreover, the saturated alkyl and alkyloxy moieties which contain more than 2 carbon atoms, mentioned in the definitions above and hereinafter, unless otherwise stated, also include the branched isomers thereof, such as, for example, the isopropyl, tert. butyl, isobutyl group etc.

Preferred compounds of general formula I are those wherein $R^2$ and $R^3$ are as hereinbefore defined, $R^1$ denotes a chlorine or bromine atom and X denotes an oxygen atom or an —NH— or —N($C_{1-3}$-alkyl)-group, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

Particularly preferred are those compounds of general formula I wherein $R^1$ denotes a chlorine or bromine atom, $R^2$ denotes a $C_{1-3}$-alkyl group substituted by a group $R_a$, where $R_a$ is as hereinbefore defined, a $C_{3-8}$-alkenyl group, a $C_{3-6}$-alkenyl group substituted by a fluorine, chlorine or bromine atom or by a trifluoromethyl group or a $C_{3-8}$-alkynyl group, X denotes an oxygen atom and $R^3$ denotes a hydrogen atom, a $C_{1-20}$-alkyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, a $C_{1-12}$-alkyl group substituted by a group $R_c$ wherein the hydrogen atoms may be wholly or partly replaced by fluorine atoms and wherein 1 to 4 methylene groups may each be replaced by an oxygen or sulphur atom, by an —NH— or —N($C_{1-3}$-alkyl)- group or by a carbonyl, sulphinyl or sulphonyl group, where $R_c$ is as hereinbefore defined, a $C_{3-8}$-cycloalkyl group wherein the hydrogen atoms may be wholly or partly replaced by fluorine atoms and wherein 1 to 4 methylene groups may each be replaced by an oxygen or sulphur atom, by an —NH— or —N($C_{1-3}$-alkyl)- group or by a carbonyl, sulphinyl or sulphonyl group, a $C_{3-20}$-alkenyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, a $C_{3-20}$-alkynyl group wherein the hydrogen atoms may be wholly or partly replaced by fluorine atoms and wherein 1 to 6 methylene groups may each be replaced by an oxygen or sulphur atom, by an —NH— or —N($C_{1-3}$-alkyl)- group or by a carbonyl, sulphinyl or sulphonyl group, or an aryl-$C_{2-6}$-alkenyl group, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

Most particularly preferred are those compounds of general formula I wherein $R^1$ denotes a chlorine or bromine atom, $R^2$ denotes a phenylmethyl group which may be substituted at the phenyl ring by a fluorine, chlorine, bromine or iodine atom or by a cyano or methoxy group, a $C_{3-8}$-alkenyl group, a $C_{3-8}$-cycloalkenylmethyl group, a $C_{3-6}$-alkenyl group substituted by a fluorine, chlorine or bromine atom or by a trifluoromethyl group or a $C_{3-8}$-alkynyl group, X denotes an oxygen atom and $R^3$ denotes a hydrogen atom, a $C_{1-20}$-alkyl group wherein the hydrogen atoms may be wholly or partly replaced by fluorine atoms and wherein 1 to 6 methylene groups may each be replaced by an oxygen or sulphur atom or by an —NH— or —N($C_{1-3}$-alkyl)- group, a $C_{1-12}$-alkyl group substituted by a group $R_c$ wherein the hydrogen atoms may be wholly or partly replaced by fluorine atoms and wherein 1 to 4 methylene groups may each be replaced by an oxygen or sulphur atom or by an —NH— or —N($C_{1-3}$-alkyl)- group, and where $R_c$ is as hereinbefore defined, a $C_{3-8}$-cycloalkyl group wherein the hydrogen atoms may be wholly or partly replaced by fluorine atoms and wherein 1 to 4 methylene groups may each be replaced by an oxygen or sulphur atom or by an —NH— or —N($C_{1-3}$-alkyl)- group, a $C_{3-20}$-alkenyl group or a $C_{3-20}$-alkynyl group, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

But particularly those compounds of general formula I, wherein $R^1$ denotes a bromine atom, $R^2$ denotes a 2-buten-1-yl or 3-methyl-2-buten-1-yl group, a 2-butyn-1-yl group or a 2-chlorophenylmethyl or 2-bromophenylmethyl group, X denotes an oxygen atom, and $R^3$ denotes a $C_{1-10}$-alkyl group or $C_{3-8}$-cycloalkyl group, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

The following compounds of general formula I are particularly preferred:

(a) methyl 2-bromo-5-formyl-3-(3-methyl-2-buten-1-yl)-3H-imidazole-4-carboxylate and (b) ethyl 2-bromo-5-formyl-3-(2-butyn-1-yl)-3H-imidazole-4-carboxylate and the salts thereof.

According to the invention the compounds of general formula I are obtained by methods known per se, for example by the following methods:

a) reduction of a compound of general formula

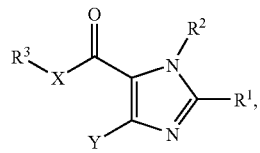

(II)

wherein $R^1$ to $R^3$ and X are as hereinbefore defined and Y denotes a carboxylic acid, carboxylic acid amide, nitrile, carboxylic acid ester, carboxylic acid thioester, carboxylic anhydride or carboxylic acid chloride group, each bound to the imidazole ring via the carboxyl carbon atom.

Reductions of the above-mentioned carboxylic acid derivatives to aldehydes are standard transformations in synthetic organic chemistry. A summary of the various possibilities can be found in Steven D. Burke, Rick L. Danheiser, Oxidizing and Reducing Agents, Weinheim: John Wiley, 1999 and in J. Seyden-Penne, Reductions by the Alumino- and Borohydrides in Organic Synthesis, Weinheim: VCH, 1991.

The following are a few representative examples:

Carboxylic acids may be converted into aldehydes, for example, with alkali metals such as lithium in ammonia or methylamine and subsequent hydrolysis of the resulting imine. Moreover, metal hydrides such as diisobutylaluminium hydride or boranes such as thexylchloro or bromoborane may be used. The reactions may be carried out at temperatures between −80° C. and 100° C., preferably between −70° C. and 40° C.

Carboxylic acid amides or nitriles may be reacted, e.g., with diisobutylaluminium hydride, lithium or sodium aluminium hydride, lithium tri-tert.-butoxyaluminium hydride and diaminoaluminium hydrides in solvents such as tetrahydrofuran, ether, toluene, hexane or dichloromethane to form the corresponding aldehydes. The reactions may be carried out at temperatures between −80° C. and 100° C., preferably between −70° C. and 25° C.

Of the examples of reducing agents which are able to convert carboxylic acid esters or anhydrides into aldehydes, hydride such as diisobutylaluminium hydride, diamino-aluminium hydride, lithium tri-tert.-butoxyaluminium hydride and sodium-bis(2-methoxyethoxy)aluminium hydride in solvents such as dichloromethane, toluene or hexane may be mentioned as being particularly suitable. The reactions may be carried out at temperatures between −80° C. and 100° C., preferably between −70° C. and 0° C.

Carboxylic acid thioesters may for example be converted into aldehydes by transition metals or transition metal complexes such as, e.g., palladium or nickel, in the presence of hydrides such as trialkylsilanes or molecular hydrogen. The use of metal hydrides such as diisobutylaluminium hydride in solvents such as hexane, dichloromethane or toluene is also a generally known method of reducing thioesters to aldehydes. The reactions may be carried out at temperatures between −80° C. and 100° C., preferably between −70° C. and 25° C.

Carboxylic acid chlorides may be converted, inter alia, with hydrogen in the presence of transition metals, such as, e.g., palladium on charcoal or barium sulphate, to form the corresponding aldehydes. Sodium borohydride in dimethylformamide and tetrahydrofuran or lithium tri-tert.-butoxyaluminium hydride in diglyme are equally suitable in many cases. The reactions may be carried out at temperatures between −100° C. and 100° C. In the presence of transition metal catalysts temperatures between 0° C. and 30° C. are preferred, whereas the reactions with metal hydrides are best carried out between −30° C. and −80° C.

b) oxidation of a compound of general formula

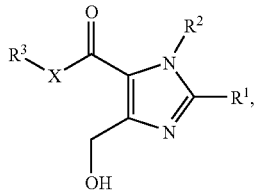

wherein $R^1$, $R^2$, $R^3$ and X are as hereinbefore defined.

The oxidation of a hydroxymethyl group to form an aldehyde is a standard reaction in synthetic organic chemistry. The oxidising agent used may be one of a number of reagents. A summary of oxidation methods and reagents for converting alcohols into aldehydes may be found in Steven D. Burke, Rick L. Danheiser, Oxidizing and Reducing Agents, Weinheim: John Wiley, 1999 and in Milos Hudlicky, Oxidation in Organic Chemistry, Washington: ACS, 1990.

Examples Include:

Oxidation with dimethylsulphoxide in the presence of for example oxalyl chloride, acetic anhydride, or sulphur trioxide-pyridine complex. Very mild oxidation can be carried out with compounds of iodine at high oxidation stages such as in so-called Dess-Martin-Periodinane. Oxidation by dehydrogenation by means of a transition metal or transition metal salt, such as, e.g., copper oxide, palladium acetate or Raney nickel, is also possible. N-iodine, N-bromine, or N-chlorosuccinimide are similarly suitable oxidizing agents for the above-mentioned transformation. Oxidation with metals at high oxidation stages or the complexes and salts thereof, such as, e.g., manganese dioxide, barium manganate, pyridinium chlorochromate, pyridinium dichromate, potassium or sodium dichromate, cerium ammonium nitrate, silver carbonate, lead tetraacetate or tetrapropylammonium perruthenate are also widely useable. The metals may be used in stoichiometric amounts or in catalytic amounts when used in the presence of a suitable co-oxidant, such as for example N-methylmorpholine-N-oxide, sodium hypochloride or sodium bromate. The choice of solvent depends on the reagent, but in many cases tetrahydrofuran, ether, dioxane, toluene, hexane, dichloromethane, ethyl acetate, sulpholane or dimethylformamide are suitable. The reactions may be carried out at temperatures between −80° C. and 100° C. Preferably the reactions are carried out between 0° C. and 60° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known, per se (cf. Allinger N. L. and Eliel E. L. in "Topics in Stereochemistry", Vol. 6, Wiley Interscience, 1971), into their optical antipodes and compounds of general formula I with at least 2 asymmetric carbon atoms may be resolved into their diastereomers on the basis of their physical-chemical differences using methods known, per se, e.g., by chromatography and/or fractional crystallization, and, if these compounds are obtained in racemic form, they may subsequently be resolved into the enantiomers as mentioned above.

The enantiomers are preferably separated by column separation on chiral phases or by re-crystallization from an optically active solvent or by reacting with an optically active substance which forms salts or derivatives such as, e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Moreover, the compounds of formula I obtained may be converted into the salts thereof. Suitable acids include for example hydrochloric acid, hydrobromic acid, sulphuric acid, methanesulphonic acid, phosphoric acid or formic acid.

In addition, if they contain a carboxy group, the new compounds of formula I thus obtained may, if desired, be converted into the salts thereof with inorganic or organic bases. Suitable bases include for example sodium hydroxide, potassium hydroxide, arginine, cyclohexylamine, ethanolamine, diethanolamine, and triethanolamine.

The compounds of general formulae II and III used as starting materials are either known from the literature or may be obtained by methods known from the literature (cf. Examples 1 and 2).

In addition to the process for preparing the compounds of general formula I the invention also relates to the use of the compounds of general formula I for synthesising imidazo[4, 5-d]pyridazin-4-ones of general formula IV according to Diagram 1 and the overall process for preparing imidazo[4,5-d] pyridazin-4-ones of general formula IV starting from commercially obtainable imidazole derivatives. The access to compounds of general formula I described here combined with their further reaction with hydrazines results in an extremely efficient and variable method of synthesising imidazo[4,5-d]pyridazin-4-ones of type V (Diagram 2), which are very good inhibitors of dipeptidylpeptidase IV (DPP IV) and can be used to treat diabetes. The method described makes it possible to obtain a wide and efficient variation in the substituents $R^1$, $R^2$ and $R^4$ of the imidazo[4,5-d]pyridazin-4-ones, making it possible to optimise all the substituents in the light of particular biological activities which are desirable or undesirable. The option of varying $R^1$ and $R^4$ at a late stage of the synthesis sequence constitutes a significant advantage over the methods described in WO 03/104229, according to which only $R^4$ can be varied at a late stage of the synthesis. The synthesis of a particular imidazo[4,5-d]pyridazin-4-one, such as, e.g., the one shown in Diagram 2, can be achieved in the manner described above in only four or five synthesis steps starting from the dimethyl 2-bromo-1H-imidazole-4,5-dicarboxylate known from the literature. In this respect, too, the method of synthesis described constitutes a significant improvement over the method of synthesis described in WO 03/104229, which would yield the same compound in nine or ten reaction steps starting from the 2-bromo-1H-imidazole-4,5-dicarboxylic acid nitrile known from the literature.

Diagram 1: Synthesis of imidazo[4,5-d]pyridazin-4-ones (IV) starting from compounds of general formula I

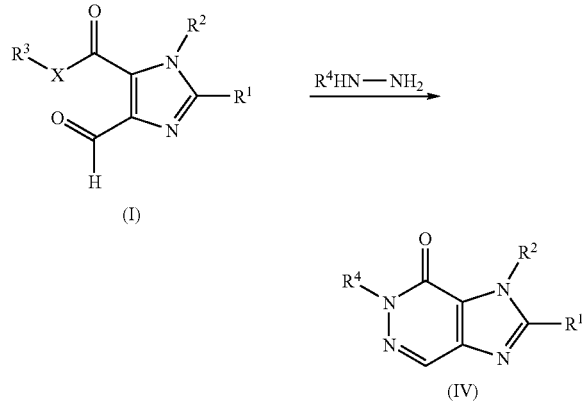

Diagram 1 shows a process for preparing imidazo[4,5-d]pyridazin-4-ones of general formula IV, wherein $R^1$ and $R^2$ are as hereinbefore defined, starting from the compound of general formula I wherein $R^1$ to $R^3$ and X are as hereinbefore defined, and a hydrazine substituted by $R^4$, where $R^4$ may denote for example a hydrogen atom, a $C_{3-8}$-alkyl group, a $C_{1-3}$-alkyl group substituted by a group $R_a$, while $R_a$ is as hereinbefore defined, a $C_{3-8}$-alkenyl or $C_{3-8}$-alkynyl group, an arylcarbonylmethyl or heteroarylcarbonylmethyl group, an arylprop-2-enyl or heteroarylprop-2-enyl group or an aryl group or heteroaryl group.

The compounds of formula IV may be synthesised by reacting compound I with a hydrazine substituted by $R^4$ or a protected hydrazine derivative thereof, such as, e.g., 1,2-bis-(t-butyldimethylsilyl)hydrazine, in a solvent such as, e.g., water, an alcohol such as methanol, ethanol, propanol, isopropanol, butanol, ether, dioxane, tetrahydrofuran, dimethylsulphoxide, dimethylformamide, dimethylacetamide, N-methylpyrrolidone, ethyl acetate, benzene or toluene. The addition of additives such as acids or bases may promote the reaction depending on X. Suitable organic acids include, e.g., toluenesulphonic acid, formic acid, acetic acid, oxalic acid or citric acid. Examples of inorganic acids which may be used are hydrochloric acid, boric acid, or sulphuric acid. Acidic clays such as, e.g., montmorillonite or Lewis acids such as for example iron chloride, lithium chloride, lithium perchlorate or magnesium chloride may also be used. Suitable inorganic bases are, e.g., lithium hydroxide, sodium hydroxide, potassium hydroxide, sodium carbonate, potassium carbonate, sodium hydrogen carbonate, aluminium oxide or sodium acetate. Organic bases such as, e.g., triethylamine, diisopropylethylamine, diazabicycloundecane, diazabicyclononane, diazabicyclooctane, pyridine, dimethylaminopyridine, N-methyl-piperidine or hexamethyldisilazane may also be suitable. It is also possible to carry out reactions in the corresponding additive without any additional solvent. The reactions may be carried out at temperatures between −80° C. and 200° C., preferably between 0° C. and 120° C. The reactions may also be carried out under microwave radiation.

The imidazo[4,5-d]pyridazin-4-ones thus obtained may be converted by suitable substitution using methods known, per se, for example, into good inhibitors of dipeptidylpeptidase IV (DPP IV), which may in turn be used in the treatment of diabetes. Diagram 2 shows, by means of an example, the synthesis of such a compound starting from a compound of general formula I.

Compounds of general formula I may be used for efficiently synthesising imidazo[4,5-d]pyridazin-4-ones of general formula IV. By suitable substitution, good DPPIV inhibitors may be obtained therefrom, as shown by the example in Diagram 2.

Diagram 2: Synthesis of a DPP IV inhibitor starting from a compound of general formula I

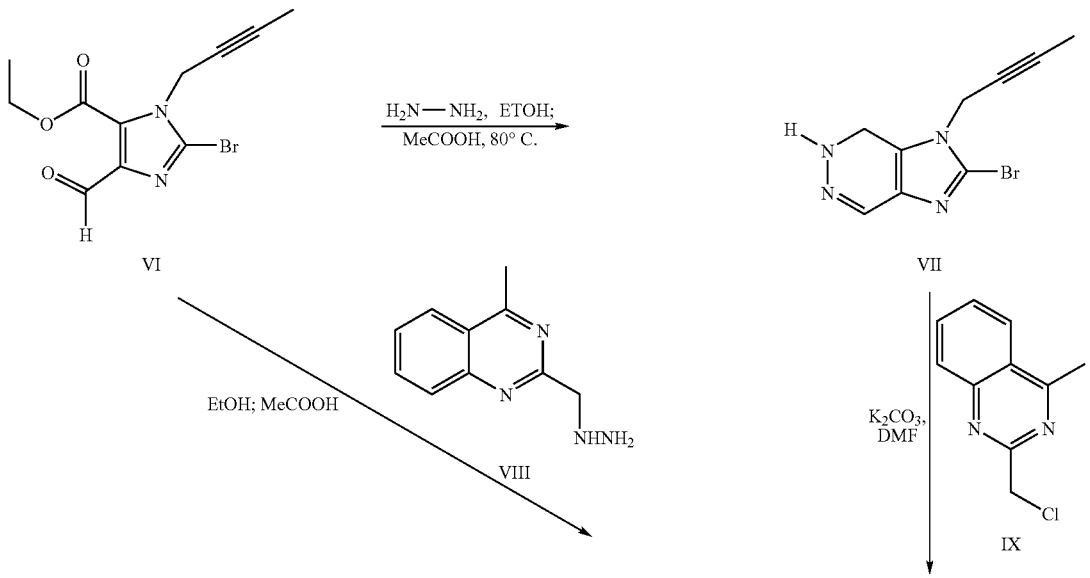

-continued

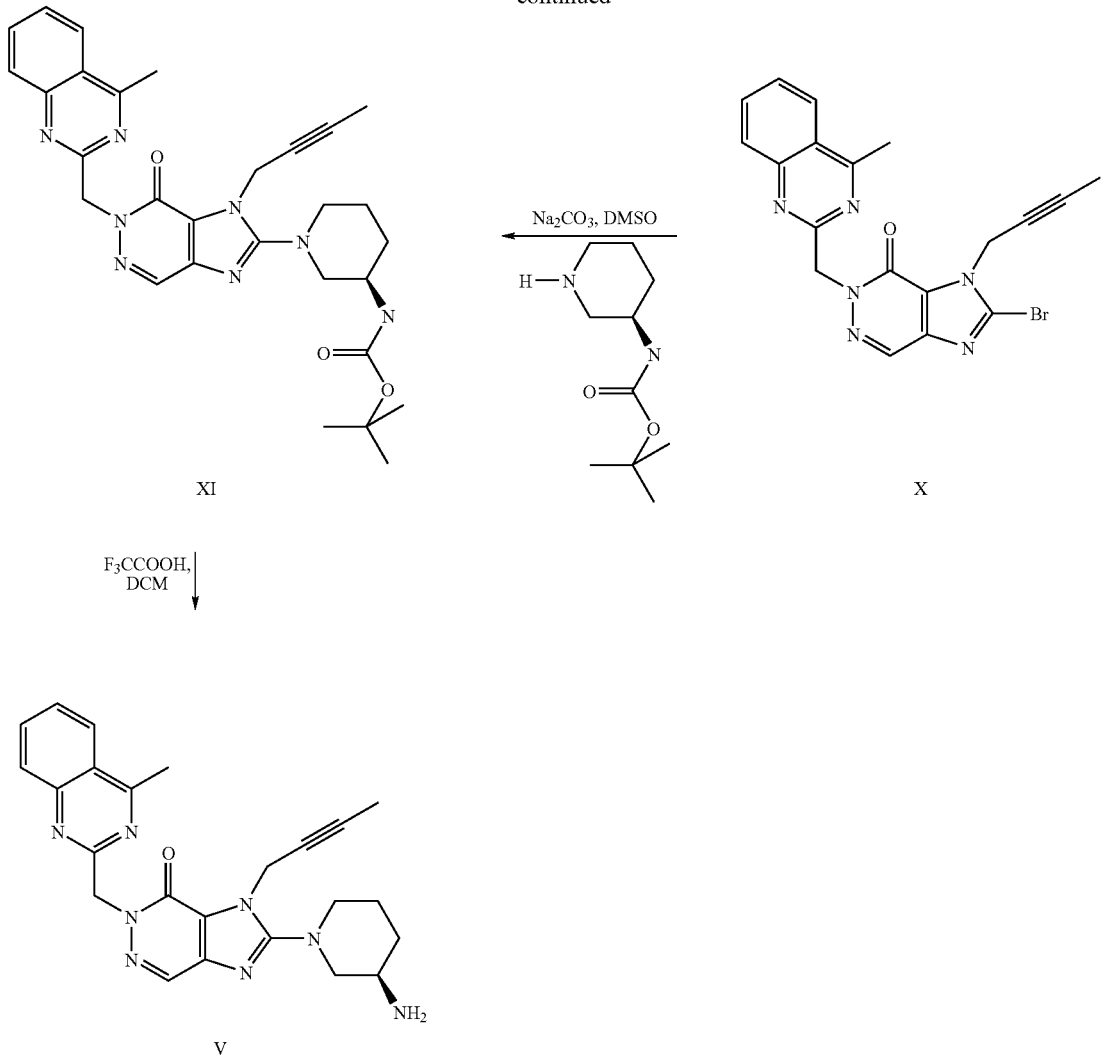

The synthesis sequence begins with the reaction of VI, which is concrete example of a compound of general formula I, with hydrazine hydrate in ethanol. After total reaction of VI with hydrazine to form the hydrazone, acetic acid is added and the solution is stirred at 100° C. Then VII is obtained in a high yield. Alkylation of VII with 2-(chloromethyl)-4-methylquinazoline IX in the presence of potassium carbonate in DMF produces X. Alternatively X may also be synthesised directly from VI with 2-(hydrazinylmethyl)-4-methylquinazoline VIII. This is done in the same way as from VI to VII. X is then reacted with (R)-3-t-butyloxycarbonylaminopiperidine in DMSO at 70° C. to produce XI, which is then obtained in a good yield. In the final reaction step the protective group in XI, t-butyloxycarbonyl, is cleaved under acidic conditions, e.g., with trifluoroacetic acid or alcoholic hydrochloric acid in dichloromethane. The DPP IV inhibitor V is thus obtained in only three or four reaction steps in consistently high yields.

The Examples that follow are intended to illustrate the invention more fully:

EXAMPLE 1

Methyl 2-bromo-3-(3-methyl-2-buten-1-yl)-5-formyl-3H-imidazole-4-carboxylate

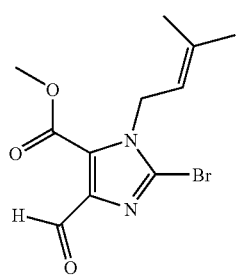

1a) dimethyl 2-bromo-1H-imidazole-4,5-dicarboxylate

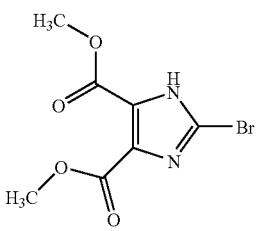

At ambient temperature 9.50 g (59.45 mmol) bromine were added dropwise to a solution of 9.90 g (53.76 mmol) dimethyl imidazole-4,5-dicarboxylate in 300 ml dichloromethane and 80 ml acetonitrile. 7.46 g (54.00 mmol) potassium carbonate was added, and the reaction mixture was stirred for 2 hours at ambient temperature. Then the dichloromethane was eliminated using the rotary evaporator and the residue was combined with a saturated solution of sodium chloride and sodium thiosulphate. It was extracted ten times with ethyl acetate, the organic extracts were dried over sodium sulphate and then the solvent was eliminated.

Yield: 12.31 g (87% of theory)

$C_7H_7BrN_2O_4$ (263.05)

Mass spectrum: $(M+H)^+$=263/265 (bromine)

1b) dimethyl 2-bromo-1-(3-methyl-2-buten-1-yl)-1H-imidazole-4,5-dicarboxylate

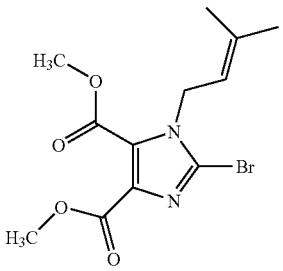

A mixture of 12.20 g (46 mmol) dimethyl 2-bromo-imidazole-4,5-dicarboxylate, 7.16 g (48 mmol) 1-bromo-3-methyl-2-butene and 7.19 g (52 mmol) potassium carbonate in 150 ml of dimethylformamide were stirred for two hours at 50° C. Then 100 ml of water were added, and the mixture was extracted three times with ethyl acetate. The extracts were dried and evaporated down. The crude product thus obtained was purified by column chromatography (silica gel; eluant: cyclohexane/ethyl acetate 4:1->2:1).

Yield: 13.52 g (89% of theory)

$C_{12}H_{15}BrN_2O_4$ (331.16)

Mass spectrum: $(M+H)^+$=331/333 (bromine)

1c) methyl 2-bromo-3-(3-methyl-2-buten-1-yl)-5-formyl-3H-imidazole-4-carboxylate

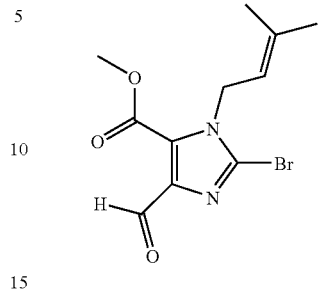

Under an argon atmosphere 35 ml (35 mmol) diisobutylaluminium hydride (1 mol/l in toluene) were added dropwise at −65° C. within 20 minutes to a solution of 9.00 g (12.18 mmol) dimethyl 2-bromo-1-(3-methyl-2-buten-1-yl)-1H-imidazole-4,5-dicarboxylate in 140 ml of tetrahydrofuran. After 1 hour at −65° C. another 5 ml (5 mmol) diisobutylaluminium hydride (1 mol/l in toluene) was added dropwise. The mixture was stirred for a further hour at −65° C. and then 20 ml of a 1:1 mixture of hydrochloric acid (1 mol/l) and tetrahydrofuran were added dropwise. After heating to ambient temperature approx. 100 ml of water was added, and the mixture was extracted three times with 70 ml of ethyl acetate. The extracts were dried over sodium sulphate, evaporated down, and the crude product thus obtained was purified by column chromatography (silica gel; eluant: cyclohexane/ethyl acetate 3:1->1:2).

Yield: 7.03 g (86% of theory)

$C_{11}H_{13}BrN_2O_3$ (301.14)

Mass spectrum: $(M+H)^+$=301/303 (bromine)

EXAMPLE 2

Ethyl 2-bromo-3-(but-2-ynyl)-5-formyl-3H-imidazole-4-carboxylate

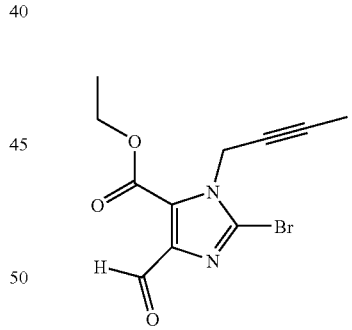

2a) diethyl 2-bromo-1H-imidazole-4,5-dicarboxylate

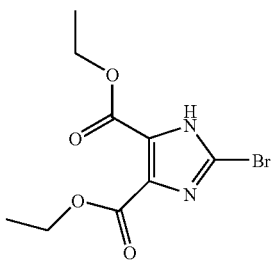

Under an argon atmosphere 3.30 g (18.54 mmol) N-bromosuccinimide were added to a solution of 2.60 g (12.25 mmol) diethyl imidazole-4,5-dicarboxylate in 30 ml acetonitrile. The solution was stirred for 24 hours in the dark at ambient temperature and then evaporated down. The residue was taken up in 150 ml of ethyl acetate and washed twice each with saturated aqueous sodium chloride solution and saturated aqueous sodium thiosulphate and once with saturated aqueous sodium chloride solution. The organic phase was dried over sodium sulphate and the solvent was removed.

Yield: 3.50 g (98% of theory)

$C_9H_{11}BrN_2O_4$ (291.10)

Rf value: 0.6 (silica gel; dichloromethane/ethanol 9:1)

Mass spectrum: $(M+H)^+=291/293$ (bromine)

2b) diethyl 2-bromo-1-(but-2-ynyl)-1H-imidazole-4,5-dicarboxylate

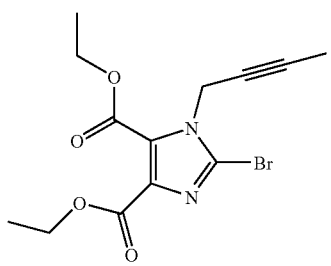

Prepared analogously to 1b from 3.50 g (12.02 mmol) diethyl 2-bromo-imidazole-4,5-dicarboxylate with 1.09 ml (12.1 mmol) 1-bromo-2-butyne and 2.07 g (15.00 mmol) potassium carbonate in 15 ml of dimethylformamide.

Yield: 3.60 g (87% of theory)

$C_{13}H_{15}BrN_2O_4$ (343.17)

Rf value: 0.8 (silica gel; dichloromethane/ethanol 9:1)

Mass spectrum: $(M+H)^+=343/345$ (bromine)

2c) ethyl 2-bromo-3-(but-2-ynyl)-5-formyl-3H-imidazole-4-carboxylate

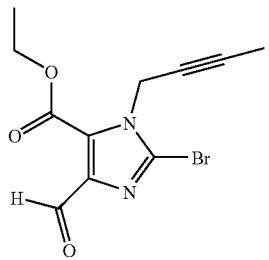

Prepared analogously to 1c from 20.00 g (58.28 mmol) diethyl 2-bromo-1-(but-2-ynyl)-1H-imidazole-4,5-dicarboxylate with 70 ml (70 mmol) diisobutylaluminium hydride in 300 ml of tetrahydrofuran.

Yield: 15.90 g (91% of theory)

$C_{11}H_{11}BrN_2O_3$ (299.12)

Mass spectrum: $(M+H)^+=299/301$ (bromine)

The following compounds may be prepared analogously to the foregoing Examples and other methods known from the literature:

| Ex. | Structure |
|---|---|
| (1) | 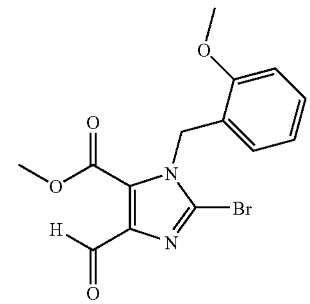 |
| (2) | 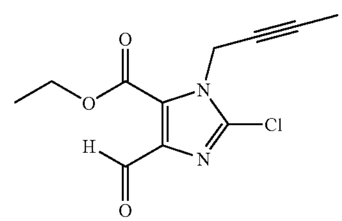 |
| (3) | 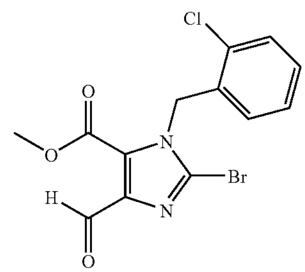 |
| (4) | 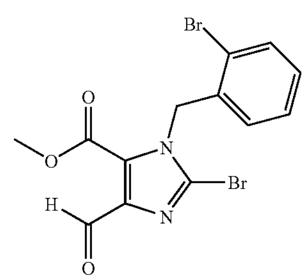 |
| (5) | 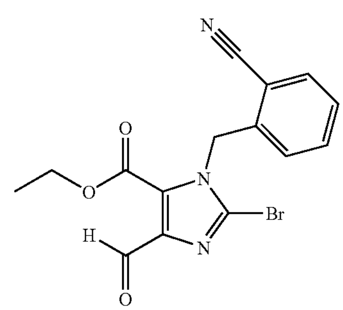 |

-continued
| Ex. | Structure |
|---|---|
| (6) | 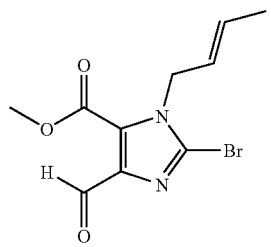 |
| (7) | 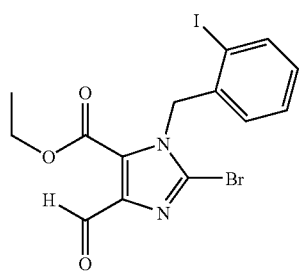 |
| (8) | 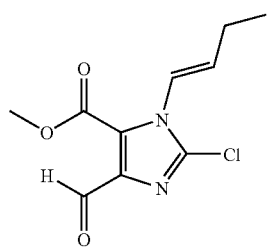 |
| (9) | 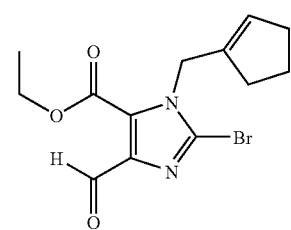 |
| (10) | 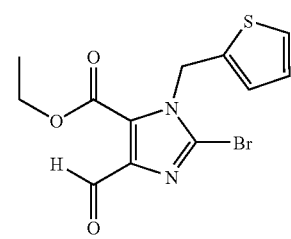 |
| (11) | 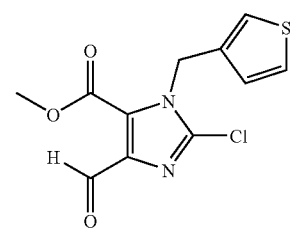 |
-continued
| Ex. | Structure |
|---|---|
| (12) | 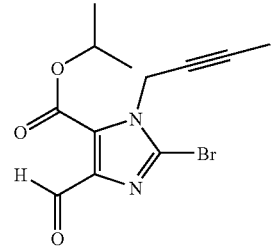 |
| (13) | 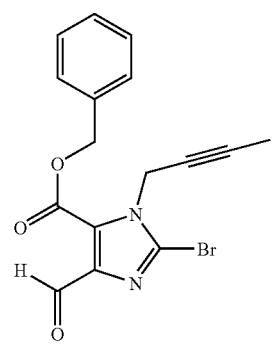 |
| (14) | 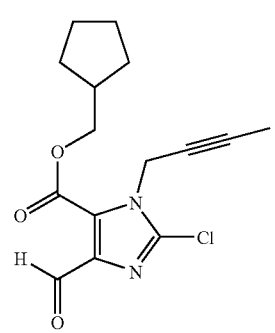 |
| (15) | 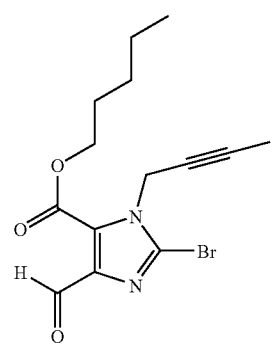 |
| (16) | 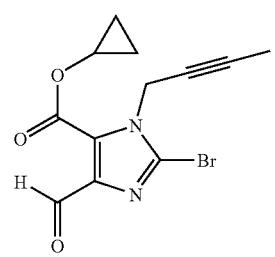 |

| Ex. | Structure |
|---|---|
| (17) | 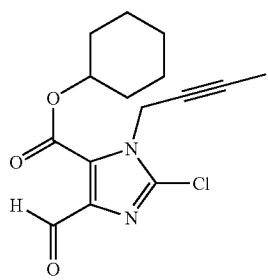 |
| (18) | 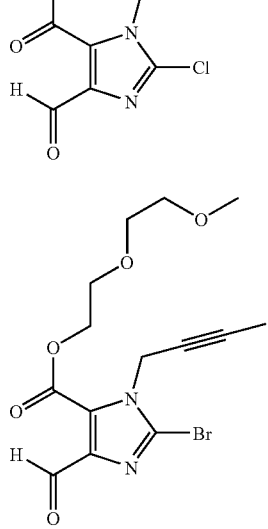 |
| (19) | 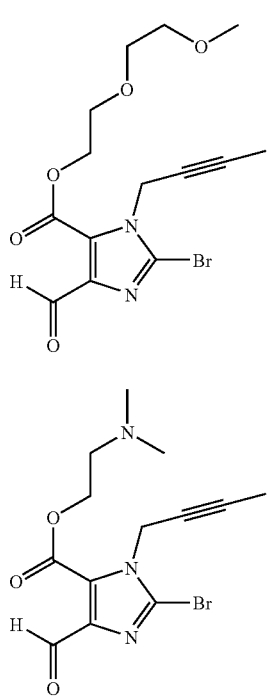 |
| (20) | 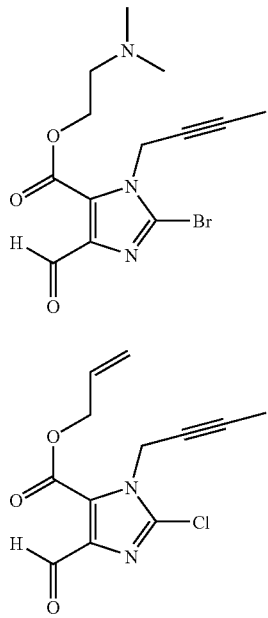 |
| (21) | 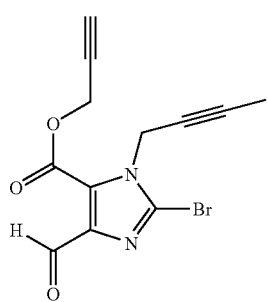 |
| Ex. | Structure |
|---|---|
| (22) | 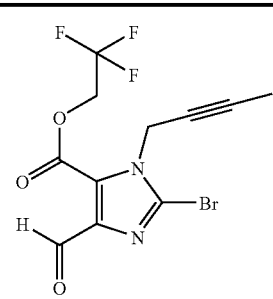 |
| (23) | 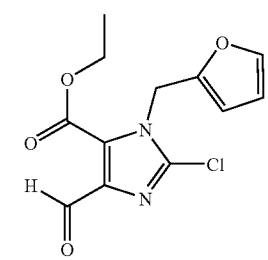 |
| (24) | 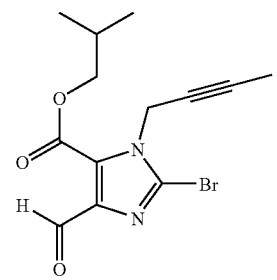 |
| (25) | 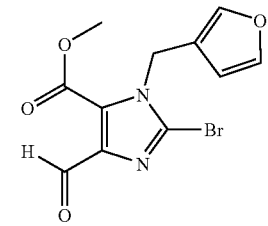 |
| (26) | 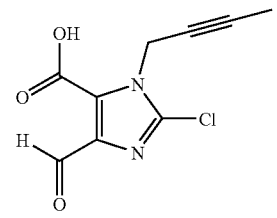 |

-continued
| Ex. | Structure |
|---|---|
| (27) | 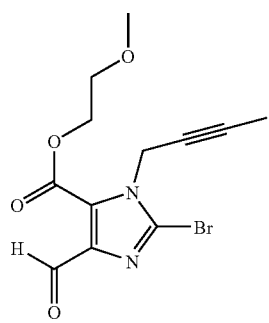 |
| (28) | 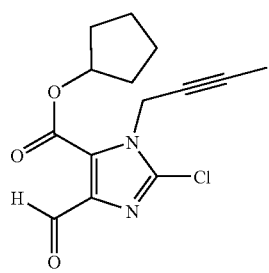 |
| (29) | 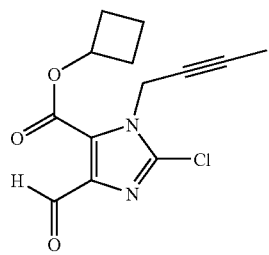 |
| (30) | 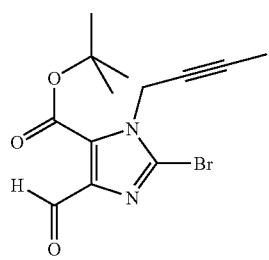 |
| (31) | 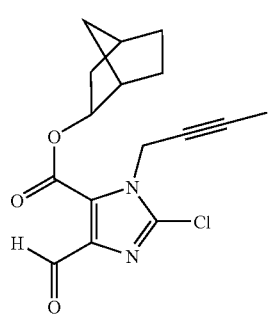 |
-continued
| Ex. | Structure |
|---|---|
| (32) | 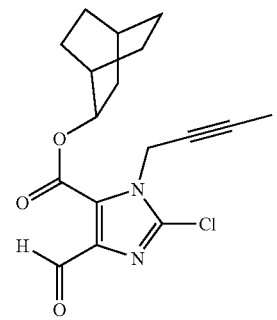 |
| (33) | 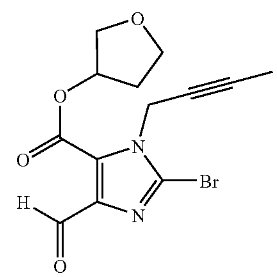 |
| (34) | 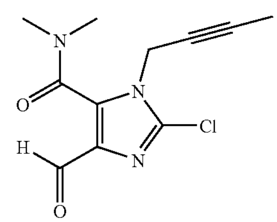 |
| (35) | 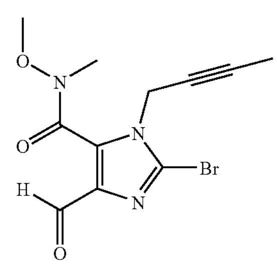 |
| (36) | 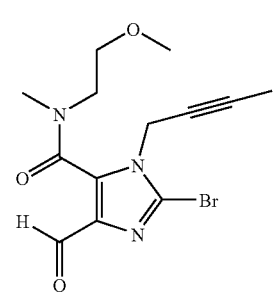 |

EXAMPLE 3 a) 2-bromo-3-(but-2-ynyl)-3,5-dihydro-imidazo[4,5-d]pyridazin-4-one (VII)

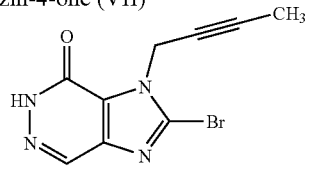

6.31 ml (0.126 mol) hydrazine hydrate were added dropwise at ambient temperature to a solution of 35.0 g (0.117 mol) ethyl 2-bromo-3-(but-2-ynyl)-5-formyl-3H-imidazole-4-carboxylate in 400 ml of ethanol. After 30 min stirring 27 ml (0.472 mol) concentrated acetic acid were added and the solution was then stirred for 1 h at 100° C. After cooling the precipitated solid was suction filtered, washed with ethanol and diethyl ether and dried. The solid was further purified by re-crystallization from EtOH.

Yield: 84% of theory.
$C_9H_7BrN_4O$ (267.09)
Mass spectrum: $(M+H)^+$=267/269 (Br)

b) 2-bromo-3-(but-2-ynyl)-5-(4-methyl-quinazolin-2-ylmethyl)-3,5-dihydro-imidazo[4,5-d]pyridazin-4-one (X)

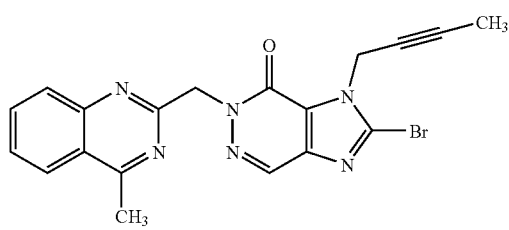

489 mg (1.5 mol) cesium carbonate were added to a solution of 300 mg (1.12 mmol) 2-bromo-3-(but-2-ynyl)-3,5-dihydro-imidazo[4,5-d]pyridazin-4-one and 344 mg (1.35 mmol) 2-chloromethyl-4-methyl-quinazoline in 4 ml of dimethylformamide and this mixture was stirred for 1 h under an argon atmosphere at 80° C. Then the mixture was diluted with 10 ml of water, the solution was cooled to approx. 10° C., the precipitate formed was suction filtered and dried and purified by column chromatography (silica gel; eluant: dichloromethane/ethanol 1:0->19:1).

Yield: 94% of theory.
$C_{19}H_{15}BrN_6O$ (423.28)
Mass spectrum: $(M+H)^+$=423/425 (Br)

c) tert-butyl (R)-{1-[1-(but-2-ynyl)-6-(4-methyl-quinazolin-2-ylmethyl)-7-oxo-6,7-dihydro-1H-imidazo[4,5-d]pyridazin-2-yl]-piperidin-3-yl}-carbamate (XI)

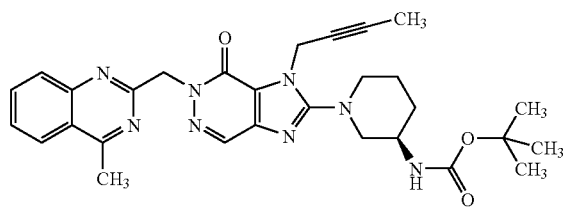

A solution of 240 mg (0.57 mmol) 2-bromo-3-(but-2-ynyl)-5-(4-methyl-quinazolin-2-ylmethyl)-3,5-dihydro-imidazo[4,5-d]pyridazin-4-one and 140 mg (0.70 mmol) tert-butyl (R)-piperidin-3-yl-carbamate in 4 ml dimethylsulphoxide was combined with 95 mg (0.90 mmol) sodium carbonate and stirred for 3 h at 80° C. Then another 50 mg tert-butyl piperidin-3-yl-carbamate was added and the mixture was stirred for a further 2 h at 80° C. After cooling to ambient temperature the mixture was combined with 10 ml of water and stirred for 30 minutes. The product thus precipitated was suction filtered, washed with 5 ml of water and dried.

Yield: 81% of theory.
$C_{29}H_{34}N_8O_3$ (542.65)
Mass spectrum: $(M+H)^+$=543 d) (R)-2-(-3-amino-piperidin-1-yl)-3-(but-2-ynyl)-5-(4-methyl-quinazolin-2-ylmethyl)-3,5-dihydro-imidazo[4,5-d]pyridazin-4-one (V)

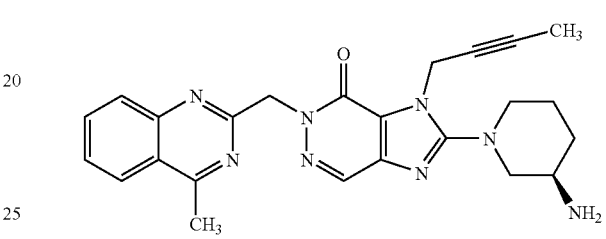

A solution of 17.2 g (31.7 mmol) tert-butyl (R)-{1-[1-(but-2-ynyl)-6-(4-methyl-quinazolin-2-ylmethyl)-7-oxo-6,7-dihydro-1H-imidazo[4,5-d]pyridazin-2-yl]-piperidin-3-yl}-carbamate in 400 ml dichloromethane was combined with 85 ml trifluoroacetic acid and stirred for three hours at ambient temperature. The mixture was evaporated to dryness at 30° C., the residue was dissolved in dichloromethane and the solution was made basic with ice-cooled saturated sodium carbonate solution. The organic phase was separated off and the aqueous phase was extracted twice more with dichloromethane. The combined organic phases were dried over sodium sulphate and the solvent was removed. The residue was purified by chromatography on silica gel (dichloromethane/methanol/ammonium hydroxide 95:5:0.1).

Yield: 89% of theory.
$C_{24}H_{26}N_8O$ (442.53)
Mass spectrum: $(M+H)^+$=443

The following compounds were obtained analogously to Example 3:

| Ex. | Structure |
|---|---|
| (1) | 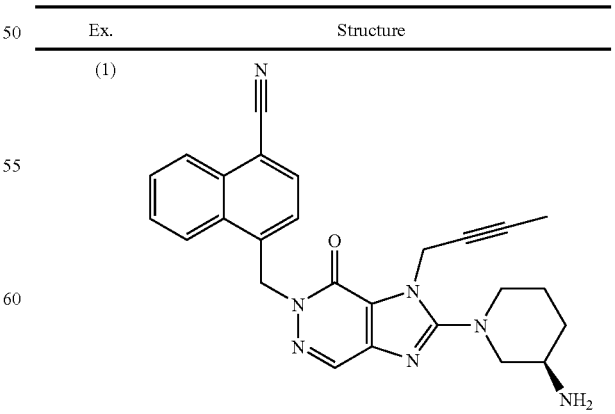<br>Mass spectrum: $(M+H)^+ = 452$ |

-continued

| Ex. | Structure |
|---|---|
| (2) | Mass spectrum: (M + H)⁺ = 427 |
| (3) | Mass spectrum: (M + H)⁺ = 429 |
| (4) | Mass spectrum: (M + H)⁺ = 439 |
| (5) | Mass spectrum: (M + H)⁺ = 453 |

-continued

| Ex. | Structure |
|---|---|
| (6) | Mass spectrum: (M + H)⁺ = 415 |
| (7) | Mass spectrum: (M + H)⁺ = 432 |
| (8) | Mass spectrum: (M + H)⁺ = 442 |
| (9) | Mass spectrum: (M + H)⁺ = 429 |

-continued

| Ex. | Structure |
|---|---|
| (10) | Mass spectrum: (M + H)$^+$ = 457 |
| (11) | Mass spectrum: (M + H)$^+$ = 405 |
| (12) | Mass spectrum: (M + H)$^+$ = 478 |
| (13) | Mass spectrum: (M + H)$^+$ = 431 |

-continued

| Ex. | Structure |
|---|---|
| (14) | Mass spectrum: (M + H)$^+$ = 428 |

I claim:
1. A process for preparing imidazo[4,5-d]pyridazin-4-ones formula (IV)

(IV)

characterised in that a compound of formula I (I)

is reacted with a hydrazine substituted by $R^4$ or a correspondingly protected hydrazine derivative,
wherein
 $R^1$ denotes a fluorine, chlorine, bromine or iodine atom,
 $R^2$ denotes:
  a $C_{3-8}$-alkyl group
  a $C_{1-3}$-alkyl group substituted by a group $R_a$,
  a $C_{3-8}$-alkenyl group,
  a $C_{3-6}$-alkenyl group substituted by a fluorine, chlorine or bromine atom or by a trifluoromethyl group,
  a $C_{3-8}$-alkynyl group,
  an aryl group or
  an aryl-$C_{2-4}$-alkenyl group,
 wherein $R_a$ denotes:
  a $C_{3-7}$-cycloalkyl group optionally substituted by one or two $C_{1-3}$-alkyl groups,
  a $C_{3-8}$-cycloalkenyl group optionally substituted by one or two $C_{1-3}$-alkyl groups,
  an aryl group or
  a heteroaryl group,
 X denotes an oxygen or sulphur atom or a nitrogen atom which is substituted by $R_b$, while $R_b$ denotes:
- a hydrogen atom,
- a hydroxy, aryloxy, arylmethyloxy, heteroaryloxy, heteroarylmethyloxy or $C_{1-10}$-alkyloxy group, while the hydrogen atoms of the alkyloxy group may be wholly or partly replaced by fluorine atoms,
- a $C_{1-10}$-alkylcarbonyl, arylcarbonyl, heteroarylcarbonyl, $C_{1-10}$-alkyloxy-carbonyl, $C_{1-10}$-alkylaminocarbonyl, di-($C_{1-10}$-alkyl)-aminocarbonyl, $C_{1-10}$-alkylsulphonyl, arylsulphonyl, heteroarylsulphonyl, $C_{1-10}$-alkylsulphinyl, arylsulphinyl or heteroarylsulphinyl group, while the hydrogen atoms of the above-mentioned $C_{1-10}$-alkyl groups may be wholly or partly replaced by fluorine atoms,
- a $C_{1-10}$-alkyl, $C_{2-10}$-alkenyl, $C_{2-10}$-alkynyl, $C_{3-7}$-cycloalkyl or $C_{5-8}$-cycloalkenyl group, while the hydrogen atoms in the above-mentioned groups may each be wholly or partly replaced by fluorine atoms and in the above-mentioned groups 1 to 4 methylene groups may each be replaced by an oxygen or sulphur atom, by an —NH— or —N($C_{1-3}$-alkyl)- group or by a carbonyl, sulphinyl or sulphonyl group,
- an aryl group or
- a heteroaryl group, or $R_b$ and $R^3$ are linked together and are closed up into a ring at the nitrogen atom, while $R_b$ and $R^3$ together denote:
- a $C_{2-7}$-alkylene group, while one or two methylene groups may each be substituted by one or two fluorine atoms or replaced by an oxygen or sulphur atom, by an —NH— or —N($C_{1-3}$-alkyl)- group or by a carbonyl, sulphinyl or sulphonyl group,
- or a $C_{4-7}$-alkenylene group, while one or two methylene groups may each be substituted by one or two fluorine atoms or replaced by an oxygen or sulphur atom, by an —NH— or —N($C_{1-3}$-alkyl)- group or by a carbonyl, sulphinyl or sulphonyl group and the double bond may be part of an aryl or heteroaryl group anellated to the ring, $R^3$ denotes:
- a hydrogen atom,
- a $C_{1-20}$-alkyl group wherein the hydrogen atoms may be wholly or partly replaced by fluorine atoms and wherein 1 to 6 methylene groups may each be replaced by an oxygen or sulphur atom, by an -NH- or -N($C_{1-3}$-alkyl)- group or by a carbonyl, sulphinyl or sulphonyl group,
- a $C_{1-12}$-alkyl group substituted by a group $R_c$ wherein the hydrogen atoms may be wholly or partly replaced by fluorine atoms and wherein 1 to 4 methylene groups may each be replaced by an oxygen or sulphur atom, by an -NH- or -N($C_{1-3}$-alkyl)- group or by a carbonyl, sulphinyl or sulphonyl group,
- a $C_{3-18}$-cycloalkyl group wherein the hydrogen atoms may be wholly or partly replaced by fluorine atoms and wherein 1 to 6 methylene groups may each be replaced by an oxygen or sulphur atom, by an -NH- or -N($C_{1-3}$-alkyl)-group or by a carbonyl, sulphinyl or sulphonyl group,
- a $C_{3-20}$-alkenyl group wherein the hydrogen atoms may be wholly or partly replaced by fluorine atoms and wherein 1 to 6 methylene groups may each be replaced by an oxygen or sulphur atom, by an -NH- or -N($C_{1-3}$-alkyl)- group or by a carbonyl, sulphinyl or sulphonyl group,
- a $C_{5-20}$-cycloalkenyl group wherein the hydrogen atoms may be wholly or partly replaced by fluorine atoms and wherein 1 to 4 methylene groups may each be replaced by an oxygen or sulphur atom, by an -NH- or -N($C_{1-3}$-alkyl)- group or by a carbonyl, sulphinyl or sulphonyl group, and wherein the double bond may be part of an aryl or heteroaryl group anellated to the ring,
- a $C_{3-20}$-alkynyl group wherein the hydrogen atoms may be wholly or partly replaced by fluorine atoms and wherein 1 to 6 methylene groups may each be replaced by an oxygen or sulphur atom, by an -NH- or -N($C_{1-3}$-alkyl)- group or by a carbonyl, sulphinyl or sulphonyl group,
- an aryl group,
- a heteroaryl group, or
- an aryl-$C_{2-6}$-alkenyl group, wherein $R_c$ denotes:
- a $C_{3-18}$-cycloalkyl group optionally substituted by one or two $C_{1-3}$-alkyl groups wherein the hydrogen atoms may be wholly or partly replaced by fluorine atoms and wherein one to two methylene groups may each be replaced by an oxygen or sulphur atom, by an -NH- or -N($C_{1-3}$-alkyl)- group or by a carbonyl, sulphinyl or sulphonyl group
- a $C_{5-18}$-cycloalkenyl optionally substituted by one or two $C_{1-3}$-alkyl groups wherein the hydrogen atoms may be wholly or partly replaced by fluorine atoms, one to two methylene groups may each be replaced by an oxygen or sulphur atom, by an -NH- or -N($C_{1-3}$-alkyl)- group or by a carbonyl, sulphinyl or sulphonyl group and the double bond may be part of an aryl or heteroaryl group anellated to the ring;
- an aryl group or
- a heteroaryl group, or, if X does not represent a nitrogen atom which is substituted by a hydroxy, aryloxy, arylmethyloxy, heteroaryloxy, heteroarylmethyloxy or $C_{1-10}$-alkyloxy group, $R^3$ may also denote an amino group which may be substituted by one or two $C_{1-3}$-alkyl groups, or, if X does not represent a nitrogen atom which is substituted by a hydroxy, aryloxy, arylmethyloxy, heteroaryloxy, heteroarylmethyloxy or $C_{1-10}$-alkyloxy group, $R^3$ may also denote a 3- to 7-membered cycloalkyleneimino group, while one to two methylene groups of the cycloalkyleneimino group may each be replaced by an oxygen atom or a carbonyl, sulphinyl or sulphonyl group, or $R^3$ and X together represent a fluorine or chlorine atom, $R^4$ denotes
- a hydrogen atom,
- a $C_{3-8}$-alkyl group,
- a $C_{1-3}$-alkyl group substituted by a group $R_a$, while $R_a$ is as hereinbefore defined,
- a $C_{3-8}$-alkenyl or $C_{3-8}$-alkynyl group,
- an arylcarbonylmethyl or heteroarylcarbonylmethyl group,
- an arylprop-2-enyl or heteroarylprop-2-enyl group or
- an aryl group or heteroaryl group;

while by the aryl groups mentioned in the definition of the above groups are meant phenyl or naphthyl groups which may be mono- to pentasubstituted independently of one another by fluorine and chlorine atoms and may be mono-, di- or trisubstituted by $R_d$, while the substituents may be identical or different and $R_d$ denotes a bromine or iodine atom, a trifluoromethyl, cyano, nitro, amino, aminocarbonyl, aminosulphonyl, methylsulphonyl, acetylamino, methylsulphonylamino, $C_{1-4}$-alkyl, $C_{1-3}$alkyl-carbonyl, cyclopropyl, ethenyl, ethynyl, hydroxy, $C_{1-4}$-alkyloxy, $C_{1-4}$-alkoxy-carbonyl, methylsulphinyl, phenylsulphinyl, methylsulphonyl, phenylsulphonyl, difluoromethoxy or trifluoromethoxy group, by the heteroaryl groups mentioned in the definition of the above-mentioned groups are meant a pyrrolyl, furanyl, thienyl, pyridyl, indolyl, benzofuranyl, benzothiophenyl, quinolinyl or isoquinolinyl group or a pyrrolyl, furanyl, thienyl or pyridyl group wherein one or two methyne groups are replaced by nitrogen atoms, or an indolyl, benzofuranyl, benzothiophenyl, quinolinyl or isoquinolinyl group wherein one to three methyne groups are replaced by nitrogen atoms, and the above-mentioned heteroaryl groups may be mono- to pentasubstituted by fluorine and chlorine atoms may be mono-, di- or trisubstituted by Rd, while the substituents may be identical or different and $R_d$ is as hereinbefore defined, by the cycloalkyl groups mentioned in the above definitions are meant both mono- and polycyclic ring systems, which are either bridged, spiro-bridged or anellated in construction, by the cycloalkenyl groups mentioned in the above definitions are meant both mono- and polycyclic ring systems, which are either bridged or anellated in construction, and have at least one C=C double bond, while, unless otherwise stated, the above-mentioned alkyl, alkenyl and alkynyl groups may be straight-chain or branched, with the exclusion of the compound wherein $R^1$ denotes a bromine atom, $R^2$ denotes a 2-butynyl group, X denotes an oxygen atom and $R^3$ denotes a methyl group, the tautomers, the enantiomers, the diastereomers, the mixtures thereof and the salts thereof.

2. A process for preparing imidazo[4,5-d]pyridazin-4-ones of formula (IV)

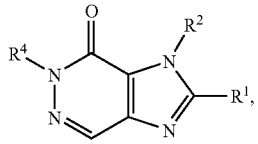

(IV)

wherein $R^1$ and $R^2$ are defined as in claim 1, characterised in that a) a compound of formula (II)

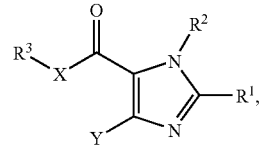

(II)

wherein $R^1$ to $R^3$ and X are defined as in claim 1 and Y denotes a carboxylic acid, carboxylic acid amide, nitrile, carboxylic acid ester, carboxylic acid thioester, carboxylic anhydride or carboxylic acid chloride group each of which is bound to the imidazole ring via the carboxyl carbon atom, is reduced, or b) a compound of formula (II)

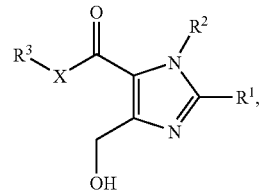

(III)

wherein $R^1$ and $R^2$ and X are defined as in claim 1, is oxidized, and c) a compound of formula (I)

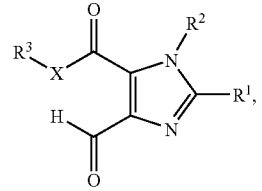

(I)

obtained according to step a) or b), wherein $R^1$ and $R^2$ and X are defined as in claim 1, is reacted with a hydrazine substituted by $R^4$ or a correspondingly protected hydrazine derivative, where $R^4$ is defined as in claim 1.

* * * * *